(12) United States Patent
Tsortos et al.

(10) Patent No.: US 8,429,953 B2
(45) Date of Patent: Apr. 30, 2013

(54) MOLECULAR CONFORMATION BIOSENSING

(75) Inventors: Achilleas Tsortos, Heraklion (GR); Georgios Papadakis, Heraklion (GR); Electra Gizeli, Voula (GR)

(73) Assignee: Foundation for Research and Technology Hellas, Crete (GR)

( * ) Notice: Subject to any disclaimer, the term of this patent is extended or adjusted under 35 U.S.C. 154(b) by 474 days.

(21) Appl. No.: 12/666,107

(22) PCT Filed: Jun. 12, 2008

(86) PCT No.: PCT/IB2008/052323
§ 371 (c)(1), (2), (4) Date: Aug. 3, 2010

(87) PCT Pub. No.: WO2008/155692
PCT Pub. Date: Dec. 24, 2008

(65) Prior Publication Data
US 2011/0048114 A1 Mar. 3, 2011

(30) Foreign Application Priority Data

Jun. 21, 2007 (GB) .................................. 0711994.4

(51) Int. Cl.
*G01N 29/02* (2006.01)

(52) U.S. Cl.
USPC ........................................ 73/64.53; 73/54.25

(58) Field of Classification Search ............... 73/64.53, 73/54.22, 54.25
See application file for complete search history.

(56) References Cited

U.S. PATENT DOCUMENTS 5,719,341 A * 2/1998 Reynolds et al. .......... 73/861.95
6,808,934 B2 * 10/2004 Mutz et al. ...................... 506/12
(Continued)

FOREIGN PATENT DOCUMENTS

| WO | WO 97/41424 | 11/1997 |
| WO | WO 03/100413 | 12/2003 |
| WO | WO 2005/050164 | 6/2005 |

OTHER PUBLICATIONS

Xiomeng et al., "Conformational chemistry of surface-attached calmodulin detected by acoustic shear wave propagation",*Molecular Biosystems*, vol. 21 No. 3-4, Mar. 2006, pp. 184-192, XP002506574.

(Continued)

*Primary Examiner* — J M Saint Surin
(74) *Attorney, Agent, or Firm* — Nixon & Vanderhye P.C.

(57) ABSTRACT

Disclosed is a method of investigating the conformation of biomolecules or changes in the conformation of biomolecules as a result of an interaction, in which biomolecules from a sample of biomolecules are adhered discretely to the sensing surface of an acoustic wave sensor operating in a liquid, and a conformation parameter which is related to the conformation of the biomolecules from the said sample which are adhered discretely to the sensing surface, but substantially independent of the resulting change in mass loading of the sensing surface, is calculated from the resulting change in the output signals of the acoustic wave sensor. The conformation parameter may the acoustic ratio or a parameter which is directly related to the acoustic ratio. There is also disclosed a method of investigating changes in the conformation of biomolecules which are adhered discretely to the sensing surface of an acoustic wave sensor operating in a liquid, in response to an interaction with an agent, by calculating a conformation parameter which is related to the change in conformation of biomolecules adhered discretely to the sensing surface as a result of an interaction with the agent, but which is substantially independent of any resulting change in mass loading of the sensing surface.

32 Claims, 4 Drawing Sheets

U.S. PATENT DOCUMENTS

| 8,227,240 B2* | 7/2012 | Elson et al. ............. 435/287.1 |
|---|---|---|
| 2004/0072208 A1* | 4/2004 | Warthoe et al. ............. 435/6 |
| 2005/0202495 A1 | 9/2005 | Kinoshita et al. |
| 2009/0001262 A1* | 1/2009 | Visser et al. ............. 250/282 |
| 2010/0207602 A1* | 8/2010 | Loverich et al. ............. 324/76.49 |

OTHER PUBLICATIONS

Zhou et al., "Human Immunoglobulin Adsorption Investigated by means of Quartz Crystal Microbalance Dissipation, Atomic Force Microscopy, Surface Acoustic Wave, and Surface Plasmon Resonance Techniques", vol. 20, No. 14, Jun. 2004, pp. 5870-5878, XP009037465.

Cooper et al., A survey of the 2001 to 2005 quartz crystal microbalance biosensor literature: applications of acoustic physics to the analysis of biomolecular interactions, *Journal of Molecular Recognition: JMR*, vol. 20, No. 3, May 2007, pp. 154-184, XP002506573.

Furtado et al., "Interactions of HIV-1 TAR RNA with Tat-derived peptides discriminated by on-line acoustic wave detector", *Analytical Chemistry*, Mar. 15, 1999, vol. 71, No. 6, pp. 1167-1175, XP002506575.

International Search Report for PCT/IB2008/052323 mailed Jan. 26, 2009.

* cited by examiner

SEQUENCE LISTING

```
<160> NUMBER OF SEQ ID NOS: 2

<210> SEQ ID NO 1
<211> LENGTH: 90
<212> TYPE: DNA
<213> ORGANISM: Artificial
<220> FEATURE:
<223> OTHER INFORMATION: Phased (Bent)

<400> SEQUENCE: 1
tcttgctggc gttcgcgacg cgaaaaaacg cgaaaaaacg cgaaaaaacg cgaaaaaacg      60
cgaaaaaacg cgttgcaggc catgctgtcc                                     90

<210> SEQ ID NO 2
<211> LENGTH: 90
<212> TYPE: DNA
<213> ORGANISM: Artificial
<220> FEATURE:
<223> OTHER INFORMATION: Outphased (Straight)

<400> SEQUENCE: 2
tcttgctggc gttcgcgacg aaacgcgcgc gcaaaaaacg cgcgcgcaaa aaacgcgcgc      60
gcaaaaaacg cgttgcaggc catgctgtcc                                     90
```

MOLECULAR CONFORMATION BIOSENSING

This application is the U.S. national phase under 35 U.S.C. 371 of International Application No. PCT/IB2008/052323 filed 12 Jun. 2008, which claims priority to British Patent Application No. GB0711994A filed 21 Jun. 2007; the entire contents of each of which are hereby incorporated by reference.

FIELD OF THE INVENTION

The invention relates to methods of determining information concerning the conformation of a sample of biomolecules using a liquid-phase acoustic wave sensor. The invention may also be used to determine information concerning a change in the conformation of a sample of biomolecules following an interaction.

BACKGROUND TO THE INVENTION

The present invention addresses the problem of determining information concerning the conformation of biomolecules and changes in the conformation of biomolecules which result from an interaction with a chemical species, such as a biological macromolecule or ligand.

The conformation of biomolecules affects, and is affected by, their chemical interactions. For example, protein binding affects the shape and activity of DNA; protein-DNA bending has been shown to facilitate the assembly of nuclear proteins complexes and play a fundamental role in the control of transcription and replication. Conversely, the intrinsic bending of DNA and the inherent deformability associated with specific base sequences can affect protein recognition and binding. The extent to which DNA is bent intrinsically and on interaction with proteins is the subject of ongoing study. Rapid methods for the detection of DNA bending would facilitate this process. Rapid methods for the detection of DNA bending would facilitate screening for potential drugs that have a mode of action involving a change in DNA conformation, for example, drugs which affect transcription and regulation by affecting protein-driven bending.

Although the invention will be discussed further with reference to the determination of information concerning the conformation of double stranded DNA, and changes in the conformation of double stranded DNA resulting from interactions of the double stranded DNA, the invention is relevant to the determination of information concerning the conformation of other biological macromolecules, such as proteins, RNA, ssDNA etc. and changes in their conformation resulting from interactions.

Commonly employed methods for measuring DNA curvature include electrophoretic mobility assays and cyclisation assays based on measurements of the rate at which DNA can form enzymatically sealed closed circles. However, it can be difficult to interpret the results of these assays. Three-dimensional crystal structures of DNA-protein complexes provide detailed insight into the mechanism of protein-driven DNA bending, but this information is only available after a long and labour-intensive process. Solution-based structural analysis via NMR will likewise provide detailed information, but such methods are not applicable to all cases and are not suitable for rapid assays. Structural information can be obtained from atomic force microscope images, but the resolution is poor.

End-tethered DNA has been studied by fluorescence to characterise the conformation of both small and large DNA molecules. Confocal microscopy of large DNA molecules with intercalated dye has been used to provide evidence that the radius of gyration of end-tethered molecules is the same as that for molecules in solution. Fluorescence interference measurements with short DNA end-labelled with a fluorophore give a measure of the height of the fluorescent label within the DNA later, which can provide indirect evidence as to the tilt of end-labelled DNA, the shape of single-stranded DNA and the extent of hybridisation. However, a disadvantage of these techniques is that they require a label and provide only limited information concerning conformation.

Accordingly, the invention aims to provide a method of determining information concerning the conformation of biomolecules and changes in the conformation of biomolecules which result from an interaction with an agent (such as another biomolecule or a chemical entity), which is suitable for label-free sensing. The invention can be used for rapid and/or parallel screening, although it may also be used to study the conformation of a specific molecule or the change of conformation of a specific molecule following a specific interaction. Some embodiments of the invention provide real-time information concerning conformation.

Although the invention will be discussed further with reference to the determination of information concerning the conformation of biomolecules and changes in the conformation of biomolecules resulting from interactions of the biomolecules using a shear acoustic wave sensor, the invention may be performed using other types of liquid-phase acoustic wave sensor. By a "liquid-phase acoustic wave sensor" we mean an acoustic wave sensor in which the sensing surface of the acoustic wave sensor is in contact with a liquid in use.

It is known to use a shear acoustic wave sensor to investigate the properties of layers of material which are adhered to a sensing surface of the sensor. Shear acoustic wave sensors probe the response of a thin layer attached to the device surface to a mechanical displacement and are, thus, sensitive to the mechanical properties of the layer and the liquid medium which is within the penetration depth of the acoustic wave of the sensing surface. The interaction between shear mode acoustic waves and continuous, firmly attached elastic layers, such as metal films and/or homogenous viscous solutions has been comprehensively described both theoretically and experimentally. The viscosity of a surface layer of biomolecules will be dependent on, amongst other things, the conformation of the biomolecules, and it is known to determine the viscosity of a surface layer which is attached to the sensing surface of a shear acoustic wave device.

However, to date, biomolecules attached to the sensing surface of a shear acoustic wave device have been analysed as if they formed a homogenous viscoelastic layer where the measured signal includes contributions from both immobilised biomolecules and solvent molecules which are trapped in-between immobilised biomolecules. Viscoelastic layers have been modelled using the simple Maxwell or Voigt mechanical models for a viscoelastic layer, in which the layer is treated as being composed of elastic springs and viscous dashpots. These models have been used to derive information related to the viscosity and shear modulus of the film without making any quantitative reference to the specific conformation of the biomolecules within the sensed film.

The invention aims to provide a novel approach to using liquid-phase acoustic wave sensors to investigate the conformation of biomolecules, and changes in the conformation of biomolecules as a result of interactions, and a novel approach to analysing the signals produced by liquid-phase acoustic wave sensors, which facilitates the investigation of the conformation of biomolecules, and changes in the conformation of biomolecules as a result of interactions.

Within this specification and the appended claims, references to proteins, RNA, DNA or other biological macromolecules are intended to include both natural macromolecules and synthetic variants, such as proteins including non-proteinogenic residues, polynucleic acids including non-natural bases etc. The term "protein" is not intended to imply any specific minimum number of peptide residues.

SUMMARY OF THE INVENTION

According to a first aspect of the present invention there is provided a method of determining information concerning the conformation of biomolecules in a liquid sample of biomolecules comprising the steps of:
(i) providing a liquid-phase acoustic wave sensor for generating an acoustic wave, which acoustic wave sensor has a sensing surface;
(ii) making a first measurement of first and second signals, wherein the first signal is related to energy losses of an acoustic wave generated by the acoustic wave sensor and the second signal is related to the frequency or phase of oscillations of the acoustic wave generated by the liquid-phase acoustic wave sensor;
(iii) adhering biomolecules in the liquid sample discretely to the sensing surface;
(iv) making a second measurement of the first and second signals;
(v) calculating a conformation parameter from the change in the first and second signals between the first and second measurements, wherein the conformation parameter is related to the conformation of the said biomolecules which are adhered discretely to the sensing surface between the first and second measurements, but substantially independent of the change in mass loading of the sensing surface between the first and second measurements.

By "discretely" we include biomolecules which are adhered to the sensing surface such that they can be validly modelled using a mathematical relation which assumes minimal or no interaction between adjacent adhered biomolecules. Accordingly, by adhering a sample of biomolecules discretely to the sensing surface and calculating the conformation parameter using a mathematical relation which assumes minimal or no interaction between adjacent adhered biomolecules, a conformation parameter which is independent of the mass loading can be calculated. This contrasts with known calculations which treat biomolecules on the sensing surface as part of a viscoelastic layer, where the signal includes a contribution from both biomolecules and solvent molecules trapped in-between biomolecules.

As the conformation parameter is substantially independent of the mass loading of the sensing surface, the conformation parameter will be substantially independent of the amount of biomolecules which have adhered to the sensing surface. This facilitates the accurate calculation of the conformation parameter in circumstances where there may be uncertainty as to the change in mass loading of the sensing surface, for example uncertainty as to what mass of the discrete molecules binds to the sensing surface between the first and second measurements.

Preferably, the calculated conformation parameter is independent of the absolute value of the mass loading of the sensing surface, over an operating range of mass loading of the sensing surface. This can increase the accuracy of the measurement of the conformation parameter in circumstances where there is uncertainty as to absolute value of the mass loading of the sensing surface. Furthermore, this facilitates the measurement of the conformation of further biomolecules from second (and potentially subsequent) samples which are subsequently adhered discretely to the surface. For example, the amount of biomolecules which are adhered to the sample may comprise less than 10%, less than 5%, or preferably less than 2% of the maximum surface loading of biomolecules. This means that multiple (e.g. 5, 10, 50 or 100) samples of discrete biomolecules may be consecutively adhered discretely to the sensing surface, and a conformation parameter calculated in respect of each sample from measurement of the first and second signals before and after the adherence of each sample to the sensing surface.

Accordingly, the method may comprise adhering biomolecules from a second sample discretely to the sensing surface, making a third measurement of the first and second signals and calculating a second conformation parameter from the change in the first and second signals between a measurement carried out before the discrete adhesion of the further biomolecules and the third measurement, wherein the second conformation parameter is related to the conformation of the biomolecules from the second sample which are adhered discretely to the sensing surface but substantially independent of the change in mass loading of the sensing surface between the measurement carried out before the discrete adhesion of the further biomolecules and the third measurement. The measurement carried out before the adhesion of the further biomolecules may be the second measurement or may be a further measurement of the first and first signals. These steps may be further repeated with third and subsequent samples of biomolecules.

The method may be used to determine information about the conformation of the biomolecules which are attached discretely to the surface. The method may be used to determine information about a change in the conformation of biomolecules as a result of an interaction with an agent (such as another biomolecule or a chemical species), by comparing the calculated conformation parameter following the adherence of a measurement sample of biomolecules which have undergone an interaction with a control conformation parameter calculated following the adherence of a control sample of biomolecules which have not undergone the interaction, or which have undergone a different interaction. The adherence of a sample of biomolecules which have undergone an interaction to a sensing surface and the adherence of a sample of biomolecules which have not undergone an interaction to a sensing surface may take place simultaneously, consecutively (in either order), or at different times, on the same sensing surface or different sensing surfaces. The method may involve making a quantitative measurement of changes in conformation resulting from a particular interaction. The method may involve making a qualitative measurement of changes in conformation resulting from a particular interaction, for example, the method may be used to determine whether a change in conformation resulted from a particular interaction.

The method may be used to establish information about the conformation of the biomolecules which were brought into contact with the sensing surface by relating the calculated conformation parameter to the conformation or range of conformations which could have lead to the calculated conformation parameter. The calculated conformation parameter may be related to the conformation or range of conformations which could have lead to the calculated conformation parameter using a theoretically and/or empirically derived relationship. The calculated conformation parameter may be related to a shape parameter which describes the shape of the adhered biomolecules. The calculated conformation parameter and/or shape parameter where relevant, may be used to predict the conformation of the biomolecules or the change in conformation of biomolecules as a result of an interaction.

Typically, the first signal is related to viscous losses within medium close to the sensing surface, but not the mass loading of the sensing surface, and the second signal is related primarily to the mass loading of the sensing surface. Typically, the viscous losses within medium close to the sensing surface are related, among other things, to the conformation of the biomolecules which are adhered discretely to the sensing surface.

The first signal which is related to energy losses of the acoustic wave may be related to (e.g. proportional to) the amplitude of the acoustic wave. The first signal may be related to (e.g. proportional to) the dissipation of the acoustic wave. The first signal may be related to electrical circuit analogue parameters such as the impedance, admittance or bandwidth parameters of the acoustic sensor.

The liquid-phase acoustic wave sensor may be a Bulk Acoustic Wave type device, such as a Quartz Crystal Microbalance or Thickness Shear Mode resonator. In this case, the second signal will typically be related to the frequency of oscillation of the liquid-phase acoustic wave sensor and the first signal will typically be related to the energy dissipation of the wave generated by the acoustic wave sensor.

The liquid-phase acoustic wave sensor may be an acoustic wave sensor which generates a shear wave; such Surface Acoustic Wave type devices can employ interdigitated transducers to generate a shear wave, such as a Love wave, Surface Skimming Bulk Wave, Acoustic Plate Mode, Bleustein-Gulyaev wave or Surface Transverse Wave. In this case, the first signal will typically be related to the amplitude of the surface acoustic wave which is generated and the second signal will typically be related to the phase (sometimes expressed as a frequency) of the surface acoustic wave which is generated.

The shear acoustic wave sensor may be a non-IDT based device such as a device employing an electromagnetically excited shear acoustic wave.

The liquid-phase acoustic wave sensor may be an acoustic wave sensor using a thin membrane to excite an acoustic wave in a configuration known as Flexural Plate Wave or Lamb wave device.

Preferably, the step of calculating a conformation parameter from the change in the first and second signals between the first and second measurements uses a relationship between the conformation parameter and the first and second signals which assumes no or minimal interaction between adjacent adhered biomolecules. For example, it may assume that the applicable Huggins constant is zero, or alternatively close to zero.

Preferably, the conformation parameter is the acoustic ratio, or a parameter which is directly related to the acoustic ratio. The acoustic ratio is the ratio of the change in amplitude or energy dissipation of the acoustic wave, or an equivalent parameter related to energy losses by way of the acoustic wave generated by the acoustic wave sensor, to the change in frequency or phase of the acoustic wave. Accordingly, if the first signal equals the amplitude or energy dissipation of the acoustic wave and the second signal equals the phase or frequency of the acoustic wave, the acoustic ratio equals the change in the first signal divided by the change in the second signal. In practice, the first signal may not be equal to the amplitude or energy dissipation of the acoustic wave, but instead by a function of (e.g. proportional to) the amplitude or energy dissipation of the acoustic wave and the second signal may be a function of (e.g. proportional to) the phase or frequency of the acoustic wave. One skilled in the art can readily take these mathematical relationships into account when preparing an algorithm to calculate the acoustic ratio or a parameter which is directly related to the acoustic ratio. The acoustic ratio may be related to the conformation of the biomolecules using a theoretical relationship and/or an empirical relationship. The acoustic ratio of model biomolecules of known or predicted conformation may be measured and used for the purposes of comparison.

In some applications, the conformation parameter may be compared with a predetermined value or range of values. For example, when screening many chemical species against samples of biomolecules it may be necessary simply to determine that, in one or more cases, the conformation parameter is different to the conformation parameter one would expect if no interaction which caused a change in the conformation of the sample of biomolecules had taken place.

The biomolecules may comprise polynucleotides, for example single stranded or double stranded DNA. The sensing surface may comprise a binding agent which binds non-specifically to a class of biomolecules, a recognition molecule which specifically binds to the biomolecules, a binding agent which binds non-specifically to a tag which is attached to the biomolecules or a recognition molecule which specifically binds to a tag which is attached to the biomolecules.

The invention extends in a second aspect to a method of screening a plurality of test agents (e.g. proteins or chemical entities) to investigate their effect on the conformation of a target biomolecule as a result of the interaction between the test agent and the target biomolecule, comprising the steps of introducing a plurality of test agents to samples of target biomolecules, calculating a conformation parameter relating to each sample of target biomolecules by the method of the first aspect, and analysing the calculated conformation parameter relating to each sample to assess the effect of the test agent on the conformation of the target biomolecule. The method may, for example, be used to investigate whether a test agent has caused a change to the conformation of a sample of target biomolecules, whether a test agent has caused a specific change to the conformation of a sample of target biomolecules, or whether a test agent has caused a change to the conformation of a sample of target biomolecules which is different to a change in the conformation of a sample of target biomolecules following an interaction with a control test agent.

Biomolecules from the samples of target biomolecules may be adhered discretely to the same sensing surface in turn, with measurements of the first and second signals taking place between the adherence of each sample to the sensing surface. An array of acoustic wave sensors having separate sensing surfaces, or one acoustic wave sensor having multiple channels within the same sensing area, may be used to analyse the effects of a plurality of different test agents on samples of target biomolecules at once. Both of these techniques may be combined to screen many test agents.

The invention extends in a third aspect to a method of screening a plurality of samples of different biomolecules (e.g. different double stranded DNA molecules or proteins) to investigate the effect of a test agent (e.g. a protein or chemical entity) on the conformation of the biomolecules in the plurality of samples of different biomolecules, comprising the steps of introducing test agent to the plurality of samples of different biomolecules, calculating a conformation parameter relating to each sample of target biomolecules by the method of the first aspect, and analysing the calculated conformation parameter relating to each sample to assess the effect of the test agent on the conformation of the biomolecules in the sample.

The method may, for example, be used to investigate whether a test agent has caused a change to the conformation of the biomolecules in a sample, or whether a test agent has caused a specific change to the conformation of target biomolecules in a sample. The method may comprise the step of comparing the calculated conformation parameter in respect of a sample of biomolecules which has not been brought into contact with the test agent and the calculated conformation parameter in respect of a sample of biomolecules which has been brought into contact with the test agent.

According to a fourth aspect of the present invention there is provided biosensing apparatus for determining information concerning the conformation of biomolecules, in a liquid sample of biomolecules, the apparatus comprising a liquid-phase acoustic wave sensor for generating an acoustic wave, the acoustic wave sensor having a sensing surface which is operable to generate first and second signals, wherein the first signal is related to energy losses of an acoustic wave generated by the acoustic wave sensor and the second signal is related to the frequency or phase of oscillations of the acoustic wave generated by the acoustic wave sensor, the apparatus further comprising data processing apparatus which is adapted to calculate a conformation parameter from the change in the first and second signals between a first measurement and a second measurement, wherein the conformation parameter is related to the conformation of the said biomolecules which are adhered discretely to the sensing surface between the time when the first measurement is taken and the time when the second measurement is taken, but substantially independent of the change in mass loading of the sensing surface between the first and second measurements.

According to a fifth aspect of the present invention there is provided a method of determining information concerning changes in the conformation of biomolecules as a result of their interaction with an agent comprising the steps of:
(i) providing a liquid-phase acoustic wave sensor for generating an acoustic wave, which acoustic wave sensor has a sensing surface in contact with a liquid, with biomolecules adhered discretely to the sensing surface;
(ii) making a first measurement of first and second signals, wherein the first signal is related to energy losses of an acoustic wave generated by the acoustic wave sensor and the second signal is related to the frequency or phase of the acoustic wave generated by the acoustic wave sensor;
(iii) introducing the agent to the biomolecules which are adhered discretely to the sensing surface;
(iv) making a second measurement of the first and second signals; and
(v) calculating a conformation parameter from the change in the first and second signals between the first and second measurements, wherein the conformation parameter is related to the change in conformation of adhered biomolecules which change conformation between the first and second measurements, as a result of their interaction with the agent, but substantially independent any change in mass loading of the sensing surface between the first and second measurements.

Thus, the method can be used to establish a conformation parameter which is indicative of the change in conformation of biomolecules which change conformation between the first and second measurements as a result of their interaction with the agent, but which is substantially independent of any change in mass loading on the sensing surface between the first and second measurements and also independent of the proportion of biomolecules which change conformation.

Further optional features correspond to the optional features discussed above in relation to the first four aspects of the invention. In particular, the calculation of the conformation parameter and details of the first and second signals are the same as described above in relation to the first four aspects of the present invention. Typically, the conformation parameter will be the acoustic ratio.

The proportion of the biomolecules adhered to the sensing surface which change conformation may be less than 10%, less than 5%, less than 2% or less than 1% of the biomolecules adhered to the sensing surface. Thus, the procedure can be repeated by introducing further agents to the biomolecules to enable the rapid screening of a plurality of agents to assess whether they affect the conformation of the biomolecules which are adhered to the sensing surface.

The invention may extend in a sixth aspect to a method of screening a plurality of test agents (e.g. proteins or chemical entities) to investigate their effect on the conformation of a target biomolecule as a result of the interaction between the test agent and the target biomolecules, comprising the steps of introducing a plurality of test agents to samples of target biomolecules, calculating a conformation parameter relating to each sample of target biomolecules by the method of the fifth aspect and analysing the calculated conformation parameter relating to each sample to assess the effect of the test agent on the conformation of the target biomolecules.

The method may, for example, be used to investigate whether a test agent has caused a change to the conformation of a sample of target biomolecules which are adhered discretely to a sensing surface, whether a test agent has caused a specific change to the conformation of a sample of target biomolecules which are adhered discretely to a sensing surface, or whether a test agent has caused a change to the conformation of a sample of target biomolecules which are adhered discretely to a sensing surface is different to a change in the conformation of a sample of target biomolecules which are adhered discretely to a sensing surface following an interaction with a control test agent.

An array of acoustic wave sensors have separate sensing surfaces, or an acoustic wave sensor having multiple channels may be used to analyse the effect of multiple agents on samples of the same biomolecules, at the same time.

According to a seventh aspect of the present invention there is provided a method of screening a plurality of samples of different biomolecules (e.g. different double stranded DNA molecules or proteins) to investigate the effect of a test agent (e.g. a protein or chemical entity) on the conformation of the biomolecules in the plurality of samples of different biomolecules, comprising the steps of introducing test agent to the a plurality of sensing surfaces with different samples of biomolecules adhered discretely thereto, calculating a conformation parameter relating to each sample of biomolecules by the method of the fifth aspect, and analysing the calculated conformation parameter relating to each sample to assess the effect of the test agent on the conformation of the biomolecules in each sample.

The method may, for example, be used to investigate whether a test agent has caused a change to the conformation of a sample of biomolecules which are adhered discretely to a sensing surface, or whether a test agent has caused a specific change to the conformation of a sample of biomolecules which are adhered discretely to a sensing surface.

According to an eighth aspect of the present invention there is provided biosensing apparatus for determining information concerning the conformation of biomolecules, in a liquid sample of biomolecules, the apparatus comprising a liquid-phase acoustic wave sensor for generating an acoustic wave, the acoustic wave sensor having a sensing surface which is in contact with a liquid and to which a sample of biomolecules can be adhered discretely, the biosensing apparatus being operable to generate first and second signals, wherein the first signal is related to energy losses of an acoustic wave generated by the acoustic wave sensor and the second signal is related to the frequency or phase of oscillations of the acoustic wave generated by the acoustic wave sensor, the apparatus further comprising data processing apparatus which is adapted to calculate a conformation parameter from the change in the first and second signals between a first measurement and a second measurement, wherein the conformation parameter is related to the change in conformation of a proportion of biomolecules which are adhered discretely to the sensing surface between the time when the first measurement is taken and the time when the second measurement is taken, but substantially independent of the change in mass loading of the sensing surface between the first and second measurements. The apparatus can be used to measure parameters relating to changes in conformation of biomolecules resulting from an interaction with an agent by adhering a sample of the biomolecules discretely to the sensing surface and introducing the test agent to the sensing surface between the first and second measurements.

DESCRIPTION OF THE DRAWINGS

An example embodiment of the present invention will now be illustrated with reference to the following Figures in which:

FIG. 5 is a plot of the acoustic ratio ($\Delta A/\Delta Ph$) versus the % of DNA surface coverage for the 198 (•), 167 (■), 132 (♦), 75 (▲) and 20 (x) base pair double stranded DNA molecules corresponding to a contour length of 67.3, 56.8, 44.9, 25.5 and 6.8 nm, respectively. The y and x axes are equivalent to:

$$\frac{\eta_{sp}}{C_i^{surf}} \text{ or } [\eta] \text{ and } C_i^{surf};$$

Figure 6:
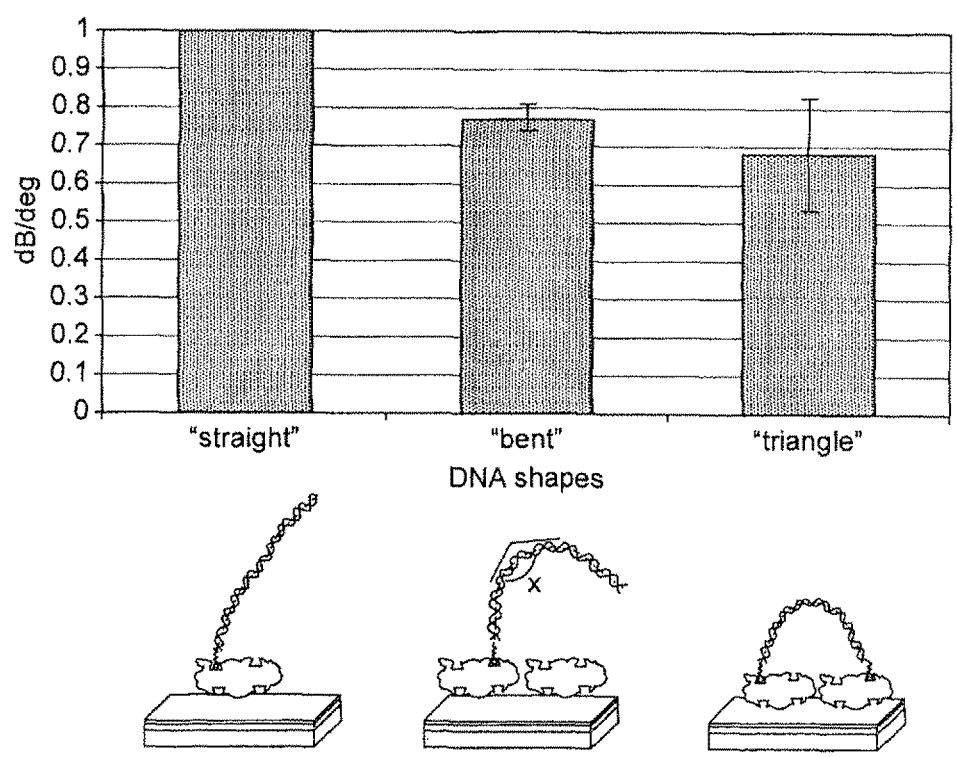
Figure 7:
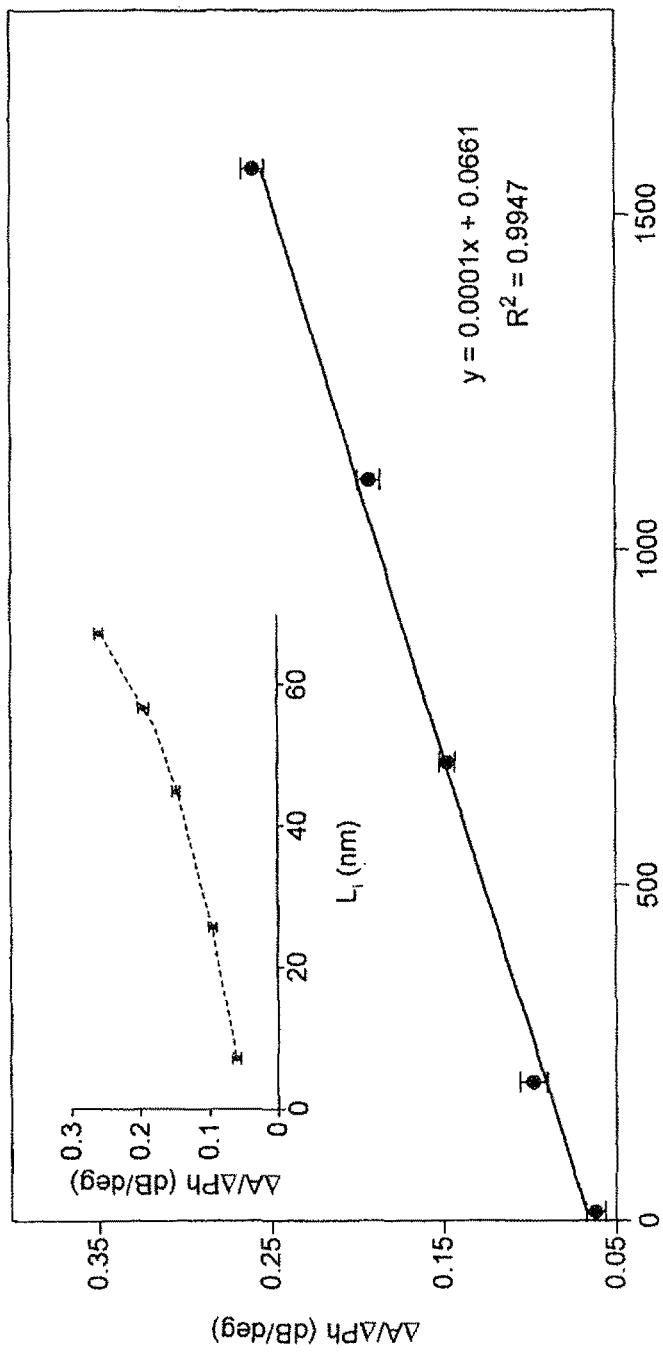

FIG. 6 is a comparison of the acoustic ratios ($\Delta A/\Delta Ph$) of the 90 base pair DNAs used with three different conformations, i.e. a "straight", "bent" and "triangle" shape; and FIG. 7 is plot of the acoustic ratio, $\Delta A/\Delta Ph$, versus contour length of straight DNA molecules (inset); with $\alpha_i$ values calculated for each $L_i$ length from Equation [6]; the straight line is a linear fit ($R^2=0.995$) of the data; the y-axis is equivalent to $$\frac{\eta_{sp}}{C_i^{surf}} \text{ or } [\eta].$$

DETAILED DESCRIPTION OF AN EXAMPLE Embodiment

Figure 1:
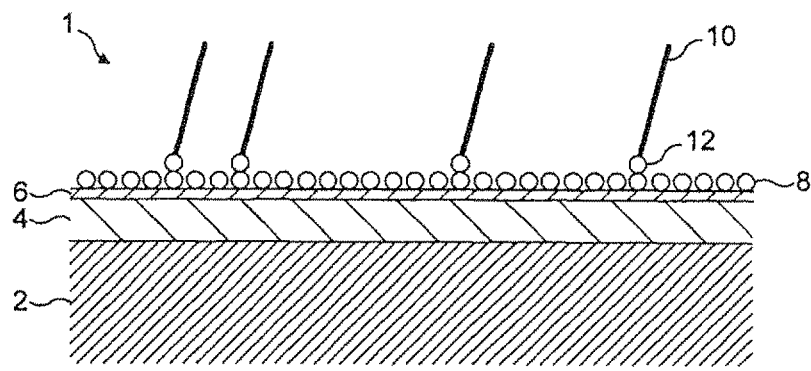
FIG. 1 is a schematic representation of the sensing layer of a Love wave surface acoustic wave device.

With reference to FIG. 1, example apparatus for investigating the conformation of double stranded DNA, or changes in the conformation of double stranded DNA following an interaction comprises a Love wave sensor 1, the construction of which is described in the Materials and Methods section below. The sensor comprises a quartz layer 2, overlaid with a polymethylmethacrylate (PMMA) layer 4 which guides shear-horizontal surface acoustic wave (SH-SAW) to the surface region, increasing the device sensitivity to surface perturbations. A sensing surface is formed by a surface gold layer 6 to which Neutravidin 8 has been adsorbed (Neutravidin is a trade mark of Pierce Biotechnology, Inc.). A network analyser drives the interdigital electrodes of the Love wave sensor and measures the amplitude (which constitutes the first signal) and phase (which constitutes the second signal) of the resulting surface acoustic wave on a continuous basis. The viscosity of a liquid which is applied to the device surface results in dissipation of the energy of the acoustic wave, measured as amplitude change in the case of a Love wave device. The penetration depth 6 of the wave inside the liquid sample is equal to the point at which the wave amplitude has decayed to 1/e of its initial value and is given by:

$$\delta = (2\eta/\pi\omega)^{1/2} \quad \text{[Equation 1]}$$

where $\eta$ is the solution viscosity, $\pi$ is the density and $\omega$ is the oscillation frequency. At the 155 MHz operating frequency of the Love wave sensor disclosed in this example embodiment, the thickness of the entrained water layer is 45 nm.

In use, a biotinylated double stranded DNA sample 10 is introduced to the liquid medium which is in contact with the sensing surface. The double stranded DNA adheres to the sensing surface by virtue of the specific interaction between biotin 12 and Neutravidin 8. The double stranded DNA molecules are attached discretely to the sensing surface. They are not attached to each other and their attachment points are spaced apart.

The change in amplitude ($\Delta A$) and phase ($\Delta Ph$) of the surface acoustic wave between a first measurement carried out before the adherence of the DNA sample to the sensing surface and a second measurement carried out after the adherence of the DNA sample to the sensing surface are determined. The acoustic ratio, $\Delta A/\Delta Ph$ is calculated, either manually or using automatic data processing apparatus, such as a computer. Surprisingly, the acoustic ratio (which functions as the conformation parameter) is related to the conformation of the biomolecules which are adhered discretely to the sensing surface but substantially independent of the change in mass loading of the sensing surface between the first and second measurements. Furthermore, the acoustic ratio is substantially independent of the absolute value of the mass loading of the sensing surface over an operating range, which typically extends from a loading of almost no biomolecules up to 50%, 75%, 90% or close to 100% surface coverage of adhered biomolecules. This facilitates the investigation of the conformation of the double stranded DNA in the sample despite uncertainties as to the amount of double stranded DNA which has adhered to the sensing surface and whether or not other samples of double stranded DNA have already been adhered to the sensing surface. This property has not been predicted or utilized by existing models describing the sensing layer as elastic and/or viscous.

Two experiments which demonstrate the effectiveness of this method for investigating the conformation of biomolecules will now be discussed. In these experiments, double stranded DNA molecules, prepared by the PCR technique and with a conformation which can be predicted from the base sequences of the DNA molecules, were bound to the Neutravidin modified device surface by using a biotin attached to the end of each DNA molecule, through a hinge of eleven carbon atoms. Experiments were performed in a flow-through system which allowed the continuous addition of consecutive DNA samples and Tris buffer in an alternating way. The attachment of DNA to the device surface was considered specific since control experiments performed with non-biotinylated DNA gave no detectable signal.

Experiment One

Figure 2:
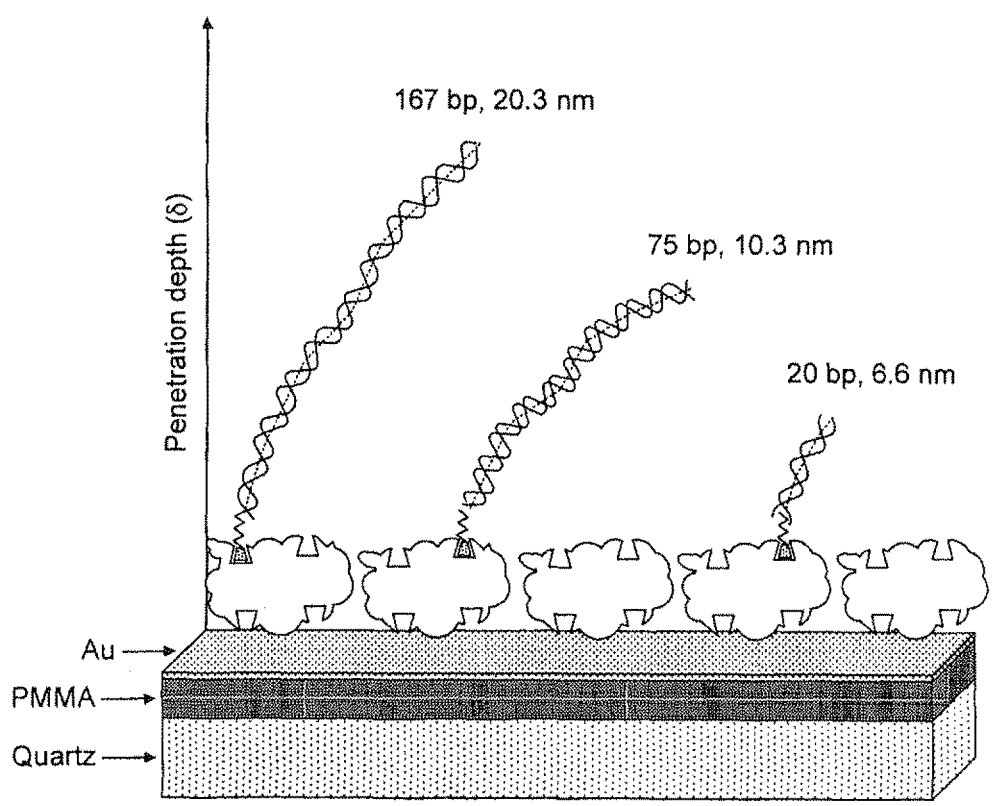
FIG. 2 is a representation, which is not to scale, of a biosensor surface/liquid interface to which generally straight double stranded DNA molecules of various lengths have been adhered via a biotin linker and a Neutravidin-modified gold surface.
Figure 3:
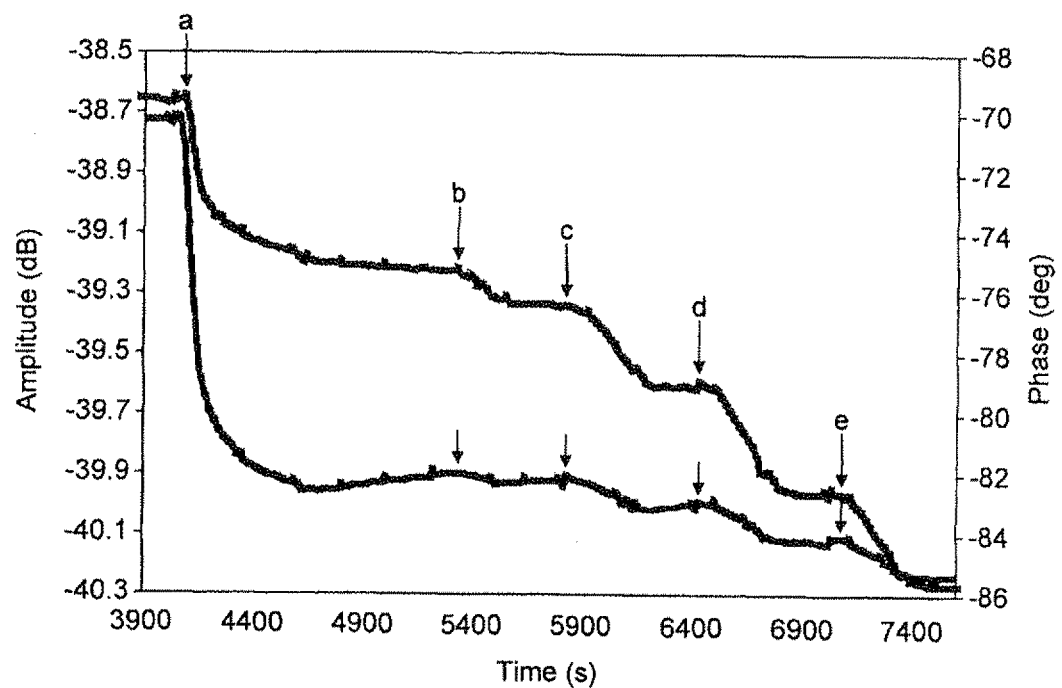
FIG. 3 is a graph which shows, in real time, the change in amplitude and phase change during the application of: (a) neutravidin 100 µg/ml, followed by 167 bp DNA samples of, (b) 1.2, (c) 2.4, (d) 3.6 and (e) 4.8 µg/ml. Buffer washing steps following each deposition are not shown in the graph.
Figure 4:
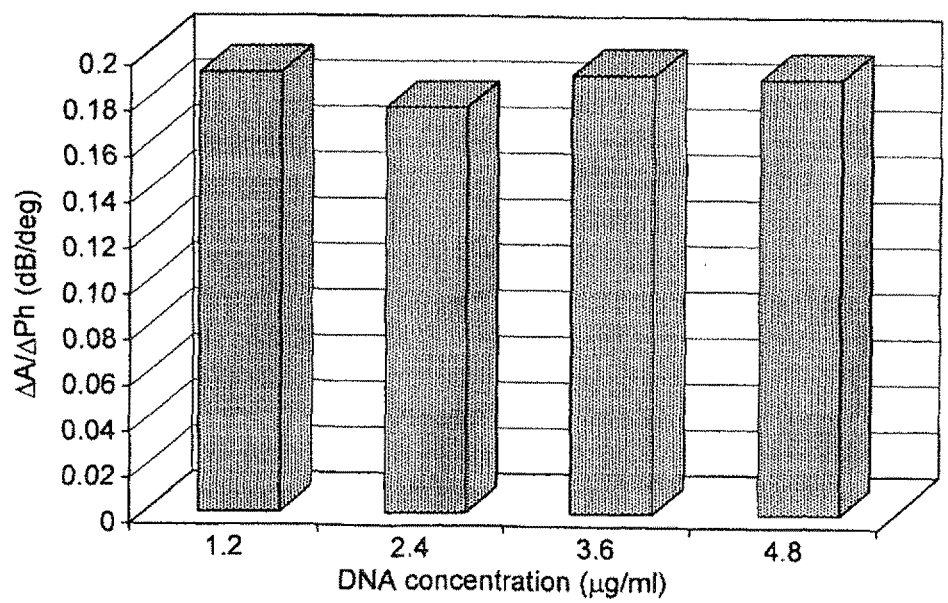
FIG. 4 is a bar chart illustrating the acoustic ratio ($\Delta A/\Delta Ph$) measured for each DNA addition shown in FIG. 3.

Acoustic Detection of Straight Double Stranded DNA Molecules of Similar Shape but Various Sizes Double stranded DNA samples applied to the surface of the acoustic wave devices had base pair lengths of 20, 75, 90, 132, 167 and 198, giving them contour lengths of 6.8, 25.5, 30.6, 44.9, 56.8 and 67.3 nm (FIG. 2). Amplitude and phase changes were measured from real-time binding curves obtained during sequential additions of 100 µl aliquots with final concentrations of DNA in the range from 1 to 8 µg/ml. Sequential additions of 100 µl aliquots at the same concentration were also used for monitoring purposes. FIG. 3 shows the change in both acoustic signals during the addition of Neutravidin (100 µg/ml) followed by the addition of four different concentrations of 167 bp DNA samples in tris buffer (1.2, 2.4, 3.6 and 4.8 µg/ml). The acoustic ratios, $\Delta A/\Delta Ph$, which were calculated from the measurements made before and after each DNA addition are plotted against the DNA concentration in FIG. 4. With the exception of the first 90 s during the first addition, the acoustic ratio was found to be constant and independent of the binding time and sample concentration. In all cases the acoustic ratio was measured at the same time, 300 s after the addition of each DNA sample. The same ratio was obtained during the saturation of the surface upon addition of 14 µg/ml of the 167 bp DNA. A characteristic constant ratio was also obtained for all the straight double stranded DNA molecules used in the experiments described herein.

DNA surface coverage was calculated as the fraction of the maximum available number of neutravidin binding sites. The later is equal to the number of Neutravidin molecules required for complete surface coverage, determined from SPR measurements to be 295 ng/cm$^2$ or 4.9 moles/cm$^2$, assuming that approximately one site is available for DNA binding on each protein molecule. A 1:1 DNA:Neutravidin ratio was assumed since electrostatic repulsion and steric hindrance considerations do not allow for higher ratios. The distance between adjacent sites is very close to that of the diameter of the hydrated negatively charged DNA rods (that is approximately 2.0 nm), as other studies have indicated.

Figure 5:
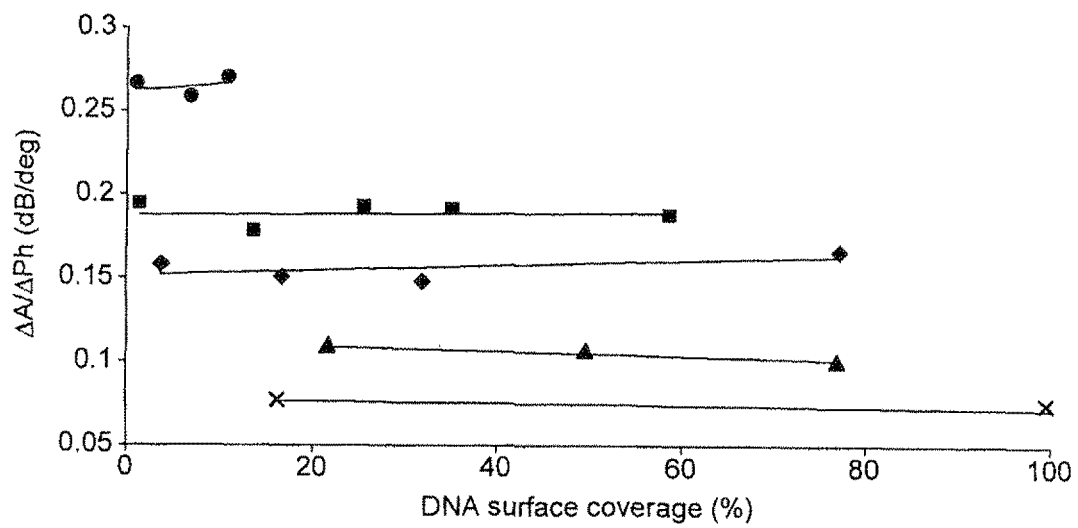

FIG. 5 gives the acoustic ratio for all double stranded DNA molecules tested in the experiments as a function of surface coverage. A striking feature of the system is that the measured acoustic ratio of each DNA molecule was independent of the device history; adding the DNA samples in random order had no effect in the measured values (data not shown). This demonstrates that measurement of the acoustic ratio reflects only intrinsic properties of each molecule and is independent of the absolute value of mass loading on the sensor surface.

Experiment Two

Acoustic Detection of DNA Molecules of Similar Size but Various Shapes

A series of three different double stranded DNA molecules were prepared with a length of 90 base pairs, and therefore substantially the same molecular weight and contour length, but with a different shape. The sequences of the DNA molecules were chosen so that the conformation of the molecule was "straight" (outphase) or "bent", with a curvature that appears half way along the molecule (phase 1). In addition, the "bent" DNA was prepared with both ends biotinylated (phase 2) and was also attached to the surface of the acoustic device to form a generally triangular structure. The acoustic ratio was measured for consecutive depositions of the three samples on the same sensing surface during the course of a single experiment and also for depositions on freshly prepared surfaces in separate experiments. The average values of the calculated acoustic ratios following experiments using four different devices are summarised in FIG. 6. For measurements carried out during one experiment, the "bent" and "triangle" DNAs had acoustic ratios which were 78% and 67%, respectively, of that of the straight DNA. This is a significant difference and demonstrates that the acoustic ratio provides information about the conformation of biomolecules.

Theoretical Model

The following theoretical model explains the relationship between acoustic ratio and the configuration of biomolecules which are attached to the sensing surface of an acoustic wave sensor. This model considers how the viscosity of the sensed volume is affected by the presence of DNA molecules at the various stages of surface coverage.

The viscosity of a liquid, by its definition, reflects its resistance to flow. The addition of large molecules in the liquid increases viscosity in a manner dependent on three parameters: concentration, size and structure, which in turn depend on the molecular weight and the conformation of these molecules. This resistance to flow is associated with the dissipation of a certain amount of energy. If changes in energy dissipation (which are measured as amplitude change in the case of a Love wave device) are taken to reflect changes in viscosity at the substrate/liquid interface within the sensed volume, then changes in this value should closely follow changes in the concentration, size and structure of the large molecules, and thus the conformation of the biomolecules.

The theory of macromolecule solution viscosity gives:

$$\frac{\eta_{sp}}{C} = [\eta] + K_H [\eta]^2 C \qquad \text{[Equation 2]}$$

where $\eta_{sp}$ is the specific viscosity of the solution at a particular concentration C, [η] is the intrinsic viscosity for a particular solute (i.e. DNA in this case) and $K_H$ is the so-called Huggins constant. (Cantor, C. R.; Schimmel, P. R. Biophysical Chemistry, Part II; Freeman: San Francisco, 1980; Tanford, C. Physical Chemistry of Macromolecules; Wiley: NY, 1961).

The following data analysis is therefore based on two assumptions. Firstly, that the change in amplitude (ΔA) corresponds to viscosity $\eta_{sp}$ (since $\eta_o$ is just a constant for the buffer solution), and, secondly, that the change in phase (ΔPh) corresponds and/or is equivalent to the macromolecule (surface) concentration. As has been demonstrated by the experiments illustrated in FIG. 5, the acoustic ratio, ΔA/ΔPh, is independent of the surface coverage i.e. surface concentration, for all the "straight" DNA molecules; the same holds true for the "bent" and "triangular" DNA molecules (data not shown). For low flow rates and non-interacting, discrete molecules $K_H$ can indeed be zero, or very nearly so, for a plot of $\eta_{sp}/C_i^{surf}$ vs $C_i^{surf}$ to be almost horizontal. Given that the capacity/possibility of lateral interactions, at least for the two-point attached "triangular" DNA, is greatly diminished, it can be assumed that $K_H$ is indeed zero for all DNA molecules used in this study.

Since ΔPh is proportional to the total mass bound per surface area, using equation [1] with $K_H=0$ we obtain:

$$\frac{\Delta A}{\Delta Ph} \propto \frac{[\eta]C^{surface}}{C^{surface}} \propto [\eta] \quad \text{[Equation 3]}$$

where $C^{surface}$ represents the concentration of a particular DNA molecule anchored on the crystal surface (area S) within the acoustically sensed volume V=Sδ while the mass is given by definition as: (# rods anchored) MW/NA=dV, d being the (constant) density of DNA, V the volume of each DNA rod and NA Avogadro's number.

In the case of straight DNA, or other molecules which can be treated as straight rods, the well known Mark-Houwink relation may be used, which correlates the intrinsic viscosity with the molecular weight of a macromolecule in a particular solvent $$[\eta]=K(MW)^\alpha \quad \text{[Equation 4]}$$

Here, α is a factor indicative of the shape, ranging from approximately 0.5 for random coils to approximately 1.8 for straight stiff rod molecules. The ds-DNA persistence length is assumed to be between 50 and 80 nm so the strands used in the present study may be safely considered as short stiff rods.

By differentiating Equation 4, using Equation 3, and observing that $$MW \propto L \propto \frac{a}{b},$$

we calculate the value of a for each straight rod DNA as:

$$\alpha = \frac{d\ln v}{d\ln\left(\frac{a}{b}\right)} \quad \text{[Equation 5]}$$

Here, the shape factors v are taken from the Simha equation, approximating the shape of stiff DNA molecules with that of a prolate ellipsoid with a and b being the major and minor semiaxes of the ellipsoid.

$$v = \frac{(a/b)^2}{5[\ln(2a/b)-1/2]} + \frac{(a/b)^2}{15[\ln(2a/b)-3/2]} + \frac{14}{15} \quad \text{[Equation 6]}$$

FIG. 7 shows a plot of the acoustic ratio, ΔA/ΔPh, versus length for each straight DNA molecule used. The curved line obtained (see inset) should become a straight line if the coefficient "α", calculated from Equation 5 is different for each length assuming the theory accurately predicts the behaviour of the system. FIG. 7 shows that an excellent straight line fit has been obtained, which validates the above approach.

In the case of bent DNA, or other biomolecules which can be treated as bent rods, the relationship of Equation 3 predicts that the energy dissipated per unit mass is proportional to the intrinsic viscosity of the relevant molecules and does not depend on the extent of surface coverage. Direct comparison of this ratio, for molecules with the same mass but different shapes, to the ratio of their respective intrinsic viscosities should be a validation for the theory employed. We have demonstrated in the experiment illustrated in FIG. 5 that this applies in the case of bent DNA strands placed in different attachment modes on the surface.

In addition, intrinsic viscosities of the "bent" and "triangle" DNA (FIG. 6) calculated based on mathematical models were found to be in excellent agreement with the experimental ratio, further validating this approach (Garcia de la Torre, J.; Bloomfield, V. Biopolymers 1978, 17, 1605-1627; Garcia de la Torre, J.; Bloomfield, V. Q. Rev. Biophys. 1981, 14, 81-139).

Thus, the acoustic ratio can be related to a shape factor, or other parameter related to the conformation of biomolecules which are adhered discretely to the sensing surface of an acoustic wave sensor.

Applications

Although the experimental examples disclosed herein relate to an analysis of the conformation of double stranded DNA, the same principles can be used to determine information concerning the conformation of other types of biomolecule, such as proteins. The acoustic ratio can be determined from the change in the output signals of an acoustic wave sensor when biomolecules are adhered discretely to the sensing surface. The acoustic ratio is typically calculated as ΔA/ΔPh when the sensing device is a Surface Acoustic Wave device. Where the sensing device is a Bulk Acoustic Wave device, the acoustic ratio can typically be calculated by dividing the change in energy dissipation of the acoustic wave by the change in frequency of the acoustic wave when biomolecules are adhered discretely to the sensing surface. Other conformation parameters which are related to the conformation of biomolecules which are adhered discretely to the sensing surface of an acoustic wave sensor could potentially be calculated by one skilled in the art for different systems.

Because the acoustic ratio has been found to be independent of the surface coverage, solution samples can be analyzed without controlling for concentration or amount, improving the accuracy of calculated conformation parameters. In addition, because the acoustic ratio has been found to be independent of the surface coverage, multiple samples can be applied sequentially to one device.

These properties have important benefits. The experiments disclosed herein exploited signal differences which would have been too small to de detected reliably with measurements on separate devices, for example, measurements using a separate device for a control. The use of a single device for multiple consecutive measurements in which a plurality of sample of biomolecules are consecutively adhered to the sensing surface facilitates rapid and/or volume screening processes.

The inherent sensitivity of the Love wave acoustic sensor discussed herein is relatively high, with a signal readily detectable from 500 μg of adsorbed DNA, although the flow system employed to deliver the sample in the example embodiment was less efficient, so that 200 ng of DNA in solution was typically required for detection. The maximum potential number of samples that may be applied before saturation of the device is therefore 100.

As well as being used to determine information concerning the conformation of the biomolecules in a sample, the methods can also be used to determine information concerning changes in the conformation of the biomolecules in a sample following an interaction, typically with an agent such as a protein or chemical entity.

In order to determine information concerning changes in the conformation, it is necessary to discretely adhere a measurement sample of biomolecules which has undergone an interaction with an agent to the sensing surface and to measure a conformation parameter, and then to compare this with a conformation parameter which has been measured or calculated in respect of a corresponding control sample of biomolecules which have not undergone the interaction with an agent. The control sample and measurement sample may be adhered consecutively to the sensing surface, in either order, or adhered to different sensing surfaces.

Thus, many test agents could be screened against equivalent samples of biomolecules to determine, for example, which test agents cause a change in the conformation of the biomolecules, which test agents cause a specific change in the conformation of the biomolecules, which test agents do not cause a change in the conformation of the biomolecules or which test agents to not cause a specific change in the conformation of the biomolecules.

Similarly, the same test agent may be screened against samples of many different biomolecules to identify biomolecules with which the test agent interacts, causing (or not causing) a particular conformational change. Except in circumstances where the various different samples could be expected to have the same conformation parameters, the method would typically also include the step of carrying out a control measurement, for example using a sample of corresponding biomolecules which has not interacted with the test agent, and comparing the conformational parameter which is calculated in each case.

The invention facilitates the investigation of interactions which affect the bending, curving or straightening of single-stranded or double stranded DNA or RNA. Changes in the conformation of DNA and RNA are important in nature and regulate processes such as transcription, replication and DNA packaging into nucleosomes. The invention can be used to investigate the implications of defects in DNA/RNA-bending proteins which are responsible for certain human diseases and for the rational design, combinatorial screening of and assessment of artificial DNA/RNA-bending proteins tailored to bend specific polynucleotide sequences to affect gene regulation for therapeutic purposes. Importantly, the invention can allow label free studies of structural changes of surface immobilized DNA/RNA molecules before and after interactions with other agents, in a quantitative way. The invention may also be applied to the development of gene therapies, new chemical entities and biologics and biochemical and physicochemical studies of DNA/RNA-ligand interactions and also to DNA/RNA biophysical studies.

Another application of the invention is to the investigation of conformation changes arising during hybridization from single stranded DNA to double stranded DNA, or conformation changes arising during DNA denaturation from double stranded DNA to single stranded DNA. Similarly, the invention may be used to investigate conformation changes relating to the formation of triple helix DNA, which can be relevant to gene regulation and some types of antisense gene therapy.

The invention is also applicable to investigations of protein conformation and interactions which affect protein conformation. Defects which alter protein folding are relevant to a number of diseases, such as cystic fibrosis, some forms of emphysema and amyloidoses, including prion diseases which are associated with the aggregation of normally soluble proteins (eg human amyloid beta protein or $PrP^C$, $PrP^{Sc}$) to insoluble fibrils. Accordingly, applications of the invention include the investigation of the conformation of proteins which are implicated in protein-folding disorders, investigation of changes in the conformation of such proteins in response to interactions with potential therapeutic agents, and the screening of potential therapeutic agents to assess their effect on the conformation of such proteins.

Materials and Methods
DNA Design and Preparation

Different sets of biotinylated and non-biotinylated primers were designed by FastPCR software and obtained from Metabion (Germany) in order to produce double-stranded DNA products of various lengths (75 bp, 132 bp, 167 bp, 198 bp) by PCR amplification. Plasmid pBR322 obtained from Minotech (Heraklio) was used as template in standard PCR reactions containing each different set of primers, mixed with 10 mM dNTPs, 1.5 mM $MgCl_2$ and 2 Units of Taq polymerase. The amplification protocol consisted of 30 cycles of an initial 45 s melting at 95° C., followed by 45 s annealing at 62° C. and 45 s extension at 72° C. PCR products were purified with a nucleospin kit (Nucleospin is a trade mark of Bioké) following the manufacturer's recommended protocol and analyzed on a 1.5% agarose gel running in TBE buffer. UV images of the products at the expected molecular weights were quantified by gel densitometry using ImageJ software from the National Institutes of Health (USA).

A 20 base-pair double stranded DNA was produced by annealing a biotinylated oligonucleotide with a 10× excess of its non-biotinylated complementary strand in an annealing buffer with 1 mM $MgCl_2$ and 20 mM Tris-HCl pH 8. The mixture was vortexed, heated-up at 95° C. for 5 min and then cooled slowly at room temperature for approximately 10 min (the SYNTHEGEN protocol).

Three 90-mer oligonucleotides were designed based on sequences from previous studies that are known to create different degrees of intrinsic curvature. Each sequence was flanked by 20 bases in order to be amplified by a PCR reaction according to the conditions described previously. The sequences of the nucleotides used in the experiments are as follows:

```
Phased (Bent)
5'-tcttgctggc gttcgcgacg cgaaaaaacg cgaaaaaacg cgaaaaaacg cgaaaaaacg cgaaaaaacg cgttgcaggc catgctgtcc-3'

Outphased (Straight)
5'-tcttgctggc gttcgcgacg aaacgcgcgc gcaaaaaacg cgcgcgcaaa aaacgcgcgc gcaaaaaacg cgttgcaggc catgctgtcc-3'
```

Some of the phased DNA was biotinylated at one end to provide bent DNA molecule which adhered at one end to the sensing surface. Another sample of the phased DNA was biotinylated at both ends so that it adhered to the sensing surface in a generally triangular conformation.

Curvature analysis of the three 90 bp products was performed using CURVE (http://www.lfd.uci.edu/gohlke/curve/) and GSVIEW software and verified by mobility differences on a 12% polyacrylamide gel under native conditions.

Preparation of Acoustic Devices

Love wave acoustic devices were prepared by photolithography using single-crystal Y-cut z-propagating 0.5 mm thick quartz, with an 100 nm gold overlayer and a 20 nm chromium adhesion layer. The input and output IDTs consisted of 192 pairs of split fingers with a periodicity of 32 μm. The operating frequency of the uncoated device was 155 MHz. A 0.4 μm thick waveguide layer of poly(methyl methacrylate) (PMMA) was deposited on the surface of the acoustic device by spin-coating the device at 4000 rpm with a 8% solution (weight solute/weight solvent) of medium molecular weight PMMA (Aldrich) in 2-ethoxyethylacetate (Aldrich). The PMMA-covered devices were heated to 195° C. for two hours to promote solvent evaporation. A 20 nm gold layer was deposited on the region between the IDTs by sputter-coating at $4 \times 10^{-2}$ mBar Argon with a Bal-Tec SCD 050 sputter-coater. The gold layer was etched immediately prior to the acoustic experiments to ensure a clean surface. Devices were re-used by etching to clean off adsorbed sample and the top layer of gold; the rate of etching was calculated and the gold was replaced by sputter-coating to maintain the 20 nm thickness.

Instrumentation and Experimental Set-Up

An Agilent E5061A network analyzer was used to measure the insertion loss (amplitude) and phase of the output signal with respect to a reference signal. The change in phase of the output signal, measured in degrees, is proportional to the change in velocity of the acoustic wave that propagates across the device; this velocity change is in turn proportional to adsorbed mass. The insertion loss, in decibels (dB), measures the change in amplitude of the acoustic wave as it travels across the device. Data was collected on a PC using LabVIEW software. A perspex flow cell and a silicone rubber gasket were used to hold the solution in place over the region between the IDTs, exposing an area of 12 $mm^2$. During experiments in which data was collected as a function of time, a 3 MHz region of the frequency spectrum near the maximum operating frequency was scanned every 20 sec to monitor the signal, with one data point collected at a fixed frequency in each scan.

A continuous flow of tris buffer (50 mM tris pH 7.5, 10 mM $MgCl_2$ and 10 mM KCl) was pumped over the surface of the gold-coated devices at a flow rate of 0.02 ml/min. The signal was allowed to equilibrate prior to the first addition and all samples were added in the same buffer. Neutravidin (Pierce) was added at a concentration of 100 μg/ml for 10 min. This was a sufficient period of time to saturate the surface with a large excess of protein. After a buffer rinse, the DNA was added at a range of concentrations specified in the experimental section above.

Further modifications and variations may be made within the scope of the invention herein disclosed.

The invention claimed is:

1. A method of determining information concerning the conformation of biomolecules in a liquid sample of biomolecules comprising the steps of:
   (i) providing a liquid-phase acoustic wave sensor for generating an acoustic wave, which acoustic wave sensor has a sensing surface;
   (ii) making a first measurement of first and second signals, wherein the first signal is related to energy losses of an acoustic wave generated by the acoustic wave sensor and the second signal is related to the frequency or phase of the acoustic wave generated by the acoustic wave sensor;
   (iii) adhering biomolecules in the liquid sample discretely to the sensing surface;
   (iv) making a second measurement of the first and second signals;

(v) calculating a conformation parameter from the change in the first and second signals between the first and second measurements, wherein the conformation parameter is related to the conformation of the said biomolecules which are adhered discretely to the sensing surface between the first and second measurements, but substantially independent of the change in mass loading of the sensing surface between the first and second measurements.

2. A method of determining information concerning the conformation of biomolecules in a sample of biomolecules according to claim 1, wherein the calculated conformation parameter is independent of the absolute value of the mass loading of the sensing surface, over an operating range of mass loading of the sensing surface.

3. A method of determining information concerning the conformation of biomolecules in a sample of biomolecules according to claim 1, further comprising the step of adhering biomolecules from a second sample discretely to the sensing surface, making a third measurement of the first and second signals and calculating a second conformation parameter from the change in the first and second signals between a measurement carried out before the discrete adhesion of the further biomolecules and the third measurement, wherein the second conformation parameter is related to the conformation of the biomolecules from the second sample which are adhered discretely to the sensing surface but substantially independent of the change in mass loading of the sensing surface between the measurement carried out before the discrete adhesion of the further biomolecules and the third measurement.

4. A method of determining information concerning the conformation of biomolecules in a sample of biomolecules according to claim 1, wherein the first signal is related to the amplitude of the acoustic wave generated by the acoustic wave sensor.

5. A method of determining information concerning the conformation of biomolecules in a sample of biomolecules according to claim 1, wherein the first signal is related to the energy dissipation of the acoustic wave generated by the acoustic wave sensor.

6. A method of determining information concerning the conformation of biomolecules in a sample of biomolecules according to claim 3, wherein the measurement carried out before the adhesion of the further biomolecules is the second measurement.

7. A method of determining information concerning the conformation of biomolecules in a sample of biomolecules according to claim 1, wherein the calculated conformation parameter is related to the conformation or range of conformations which could have lead to the calculated conformation parameter.

8. A method of determining information concerning the conformation of biomolecules in a sample of biomolecules according to claim 7, wherein the calculated conformation parameter is related to a shape parameter which describes the shape of the adhered biomolecules.

9. A method of determining information concerning the conformation of biomolecules in a sample of biomolecules according to claim 1, wherein the liquid-phase acoustic wave sensor is a Bulk Acoustic Wave type device, the second signal is related to the frequency of oscillations of the acoustic wave sensor and the first signal is related to the energy dissipation of the acoustic wave generated by the acoustic wave sensor.

10. A method of determining information concerning the conformation of biomolecules in a sample of biomolecules according to claim 1, wherein the liquid-phase acoustic wave sensor is a Surface Acoustic Wave type device, the first signal is related to the amplitude of the surface acoustic wave generated by the acoustic wave sensor and the second signal is related to the phase of the surface acoustic wave generated by the acoustic wave sensor.

11. A method of determining information concerning the conformation of biomolecules in a sample of biomolecules according to claim 1, wherein the step of calculating a conformation parameter from the change in the first and second signals between the first and second measurements uses a relationship between the conformation parameter and the first and second signals which assumes no or minimal interaction between adjacent adhered biomolecules.

12. A method of determining information concerning the conformation of biomolecules in a sample of biomolecules according to claim 1, wherein the conformation parameter is the acoustic ratio, or a parameter which is directly related to the acoustic ratio.

13. A method of determining information concerning the conformation of biomolecules in a sample of biomolecules according to claim 1, wherein the conformation parameter is compared with a predetermined value or range of values.

14. A method of determining information concerning the conformation of biomolecules in a sample of biomolecules according to claim 1, wherein the sensing surface comprises a binding agent which binds non-specifically to a class of biomolecules, a recognition molecule which specifically binds to the biomolecules, a binding agent which binds non-specifically to a tag which is attached to the biomolecules or a recognition molecule which specifically binds to a tag which is attached to the biomolecules.

15. A method of determining information concerning a change in the conformation of biomolecules in a sample of biomolecules comprising calculating a measurement conformation parameter relating to a measurement sample of biomolecules which has undergone an interaction with an agent, and calculating a control conformation parameter relating to a control sample of corresponding biomolecules which has not undergone an interaction with an agent, according to the method of claim 1 and assessing the difference between the measurement conformation parameter and the control measurement parameter.

16. A method of determining information concerning a change in the conformation of biomolecules in a sample of biomolecules according to claim 15, wherein the assessment of the difference between the measurement conformation parameter and the control measurement parameter is qualitative.

17. A method of screening a plurality of test agents to investigate their effect on the conformation of a target biomolecule as a result of the interaction between the test agent and the target biomolecule, comprising the steps of introducing a plurality of test agents to samples of target biomolecules, calculating a conformation parameter relating to each sample of target biomolecules by the method of claim 1, and analysing the calculated conformation parameter relating to each sample to assess the effect of the test agent on the conformation of the target biomolecule.

18. A method of investigating whether a test agent has caused a change to the conformation of a sample of target biomolecules, investigating whether a test agent has caused a specific change to the conformation of a sample of target biomolecules, or investigating whether a test agent has caused a change to the conformation of a sample of target biomolecules which is different to a change in the conformation of a sample of target biomolecules following an interaction with a control test agent comprising screening a plurality of test agents to investigate their effect on the conformation of a target biomolecule as a result of the interaction between the test agent and the target biomolecule by a method according to claim 17.

19. A method according to claim 17, wherein biomolecules from the samples of target biomolecules are adhered discretely to the same sensing surface in turn, with measurements of the first and second signals taking place between the adherence of each sample to the sensing surface.

20. A method according to claim 17, wherein an array of acoustic wave sensors having separate sensing surfaces or an acoustic wave sensor with multiple sensing channels are used to analyse the effects of multiple test agents on samples of target biomolecules at the same time.

21. A method of screening a plurality of samples of different biomolecules to investigate the effect of a test agent on the conformation of the biomolecules in the plurality of samples of different biomolecules, comprising the steps of introducing test agent to the plurality of samples of different biomolecules, calculating a conformation parameter relating to each sample of target biomolecules by the method of claim 1, and analysing the calculated conformation parameter relating to each sample to assess the effect of the test agent on the conformation of the biomolecules in the sample.

22. A method of screening a plurality of samples of different biomolecules to investigate the effect of a test agent on the conformation of the biomolecules in the plurality of samples of different biomolecules according to claim 21, further comprising the step of comparing the calculated conformation parameter in respect of a sample of biomolecules which has not been brought into contact with the test agent and the calculated conformation parameter in respect of a sample of biomolecules which has been brought into contact with the test agent.

23. Biosensing apparatus for determining information concerning the conformation of biomolecules in a liquid sample of biomolecules, the apparatus comprising a liquid-phase acoustic wave sensor for generating an acoustic wave, the acoustic wave sensor having a sensing surface which is operable to generate first and second signals, wherein the first signal is related to energy losses of an acoustic wave generated by the acoustic wave sensor and the second signal is related to the frequency or phase of oscillations of the acoustic wave generated by the acoustic wave sensor, the apparatus further comprising data processing apparatus which is configured to calculate a conformation parameter from the change in the first and second signals between a first measurement and a second measurement, wherein the conformation parameter is related to the conformation of the said biomolecules which are adhered discretely to the sensing surface between the time when the first measurement is taken and the time when the second measurement is taken, but substantially independent of the change in mass loading of the sensing surface between the first and second measurements.

24. A method of determining information concerning changes in the conformation of biomolecules as a result of their interaction with an agent comprising the steps of:
(i) providing a liquid-phase acoustic wave sensor for generating an acoustic wave, the acoustic wave sensor having a sensing surface in contact with a liquid, with biomolecules adhered discretely to the sensing surface;
(ii) making a first measurement of first and second signals, wherein the first signal is related to energy losses of an acoustic wave generated by the acoustic wave sensor and the second signal is related to the frequency or phase of the acoustic wave generated by the acoustic wave sensor;
(iii) introducing the agent to the biomolecules which are adhered discretely to the sensing surface;
(iv) making a second measurement of the first and second signals; and
(v) calculating a conformation parameter from the change in the first and second signals between the first and second measurements, wherein the conformation parameter is related to the change in conformation of adhered biomolecules which change conformation between the first and second measurements, as a result of their interaction with the agent, but substantially independent of any change in mass loading of the sensing surface between the first and second measurements.

25. A method of determining information concerning changes in the conformation of biomolecules according to claim 24, wherein the first signal is related to the amplitude or energy dissipation of the acoustic wave generated by the acoustic wave sensor.

26. A method of determining information concerning changes in the conformation of biomolecules according to claim 24, wherein the conformation parameter is the acoustic ratio.

27. A method of determining information concerning changes in the conformation of biomolecules according to claim 24, wherein the proportion of the biomolecules adhered to the sensing surface which change conformation is less than 10%.

28. A method of screening a plurality of test agents to investigate their effect on the conformation of a target biomolecules as a result of the interaction between the test agent and the target biomolecules, comprising the steps of introducing a plurality of test agents to samples of target biomolecules, calculating a conformation parameter relating to each sample of target biomolecules by the method of claim 24 and analysing the calculated conformation parameter relating to each sample to assess the effect of the test agent on the conformation of the target biomolecules.

29. A method of screening a plurality of test agents according to claim 28, wherein an array of acoustic wave sensors have separate sensing surfaces, or an acoustic wave sensor having multiple channels are used to analyse the effect of a plurality of different agents on samples of the same biomolecules, at the same time.

30. A method of screening a plurality of samples of different biomolecules to investigate the effect of a test agent on the conformation of the biomolecules in the plurality of samples of different biomolecules, comprising the steps of introducing test agent to the a plurality of sensing surfaces with different samples of biomolecules adhered discretely thereto, calculating a conformation parameter relating to each sample of biomolecules by the method of claim 24, and analysing the calculated conformation parameter relating to each sample to assess the effect of the test agent on the conformation of the biomolecules in each sample.

31. A method of screening a plurality of test agents according to claim 30, comprising investigating whether a test agent has caused a change to the conformation of a sample of biomolecules which are adhered discretely to a sensing surface, or whether a test agent has caused a specific change to the conformation of a sample of biomolecules which are adhered discretely to a sensing surface.

32. Biosensing apparatus for determining information concerning the conformation of biomolecules, in a liquid sample of biomolecules, the apparatus comprising a liquid-phase acoustic wave sensor for generating an acoustic wave, the acoustic wave sensor having a sensing surface which is in contact with a liquid, the biosensing apparatus being operable to generate first and second signals, wherein the first signal is related to energy losses of an acoustic wave generated by the acoustic wave sensor and the second signal is related to the frequency or phase of oscillations of the acoustic wave generated by the acoustic wave sensor, the apparatus further comprising data processing apparatus which is adapted to calculate a conformation parameter from the change in the first and second signals between a first measurement and a second measurement, wherein the conformation parameter is related to the change in conformation of a proportion of biomolecules which are adhered discretely to the sensing surface between the time when the first measurement is taken and the time when the second measurement is taken, but substantially independent of any change in mass loading of the sensing surface between the first and second measurements.

* * * * *

UNITED STATES PATENT AND TRADEMARK OFFICE
CERTIFICATE OF CORRECTION

PATENT NO. : 8,429,953 B2
APPLICATION NO. : 12/666107
DATED : April 30, 2013
INVENTOR(S) : Tsortos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 698 days.

Signed and Sealed this
Eighth Day of September, 2015

Michelle K. Lee
*Director of the United States Patent and Trademark Office*